(12) United States Patent
Stromberg

(10) Patent No.: US 9,856,601 B2
(45) Date of Patent: Jan. 2, 2018

(54) METHOD AND APPARATUS FOR ADDING STEAM FOR A STEAM EXPLOSION PRETREATMENT PROCESS

(71) Applicant: Andritz Inc., Glens Falls, NY (US)

(72) Inventor: Bertil Stromberg, Diamond Point, NY (US)

(73) Assignee: Andritz Inc., Glens Falls, NY (US)

( * ) Notice: Subject to any disclaimer, the term of this patent is extended or adjusted under 35 U.S.C. 154(b) by 327 days.

(21) Appl. No.: 14/428,182

(22) PCT Filed: Sep. 18, 2013

(86) PCT No.: PCT/US2013/060272
§ 371 (c)(1),
(2) Date: Mar. 13, 2015

(87) PCT Pub. No.: WO2014/047097
PCT Pub. Date: Mar. 27, 2014

(65) Prior Publication Data
US 2015/0233053 A1    Aug. 20, 2015

Related U.S. Application Data

(60) Provisional application No. 61/703,082, filed on Sep. 19, 2012.

(51) Int. Cl.
*D21B 1/36* (2006.01)
*D21C 1/02* (2006.01)
(Continued)

(52) U.S. Cl.
CPC ............... *D21B 1/36* (2013.01); *D21C 1/02* (2013.01); *D21C 1/10* (2013.01); *D21C 7/08* (2013.01)

(58) Field of Classification Search
CPC ............... D21C 1/02; D21C 1/10; D21B 1/36
(Continued)

(56) References Cited

U.S. PATENT DOCUMENTS

| 1,922,313 A | 8/1933 | Mason |
| 2,616,802 A | 11/1952 | Kehoe et al. |

(Continued)

FOREIGN PATENT DOCUMENTS

| CA | 1217765 B | * 2/1987 | ............... C13K 1/02 |
| CN | 2476335 Y |   2/2002 | |

(Continued)

OTHER PUBLICATIONS

The State Intellectual Property Office of the Peoples Republic of China, Notification of First Office Action, Dec. 15, 2015, pp. 1-12, SIPO, Beijing, China.
(Continued)

*Primary Examiner* — Anthony Calandra
(74) *Attorney, Agent, or Firm* — Kerri Hochgesang; Robert Joseph Hornung

(57) ABSTRACT

A method for treating cellulosic biomass feed stock including: feeding the feed stock to an upper inlet of a vertical reactor vessel, wherein the feed stock is deposited on a pile of feed stock within the vertical reactor vessel; adding heat energy to heat the feed stock by injecting steam to an upper region of the vertical reactor vessel; propelling the feed stock through an outlet in a lower region of the vertical reactor vessel by injecting steam into the biomass at, near or after the bottom outlet of the vertical reactor vessel, and moving the propelled feed stock through an expansion device, such as a steam explosion device, to subject the feed stock to a steam explosion process.

21 Claims, 1 Drawing Sheet

(51) Int. Cl.
*D21C 1/08* (2006.01)
*D21C 1/10* (2006.01)
*D21C 7/08* (2006.01)

(58) Field of Classification Search
USPC .................................. 99/323.4; 162/21, 247
See application file for complete search history.

(56) References Cited

U.S. PATENT DOCUMENTS

| | | | |
|---|---|---|---|
| 2,882,967 | A | 4/1959 | Surino |
| 5,500,083 | A | 3/1996 | Johanson |
| 5,617,975 | A | 4/1997 | Johanson |
| 5,628,873 | A | 5/1997 | Johanson |
| 8,057,639 | B2 | 11/2011 | Pschorn et al. |
| 2008/0277082 | A1 | 11/2008 | Pschorn et al. |
| 2009/0020244 | A1* | 1/2009 | Stromberg ............... D21C 1/00 162/17 |
| 2009/0221814 | A1* | 9/2009 | Pschorn ................... D21B 1/36 536/128 |
| 2010/0065128 | A1* | 3/2010 | Benson ................. B09B 3/0091 137/2 |
| 2010/0083530 | A1 | 4/2010 | Weisselberg et al. |

FOREIGN PATENT DOCUMENTS

| | | |
|---|---|---|
| EP | 2177280 | 4/2010 |
| KR | 20010048481 | 6/2001 |
| WO | 2011006854 | 1/2011 |

OTHER PUBLICATIONS

Bohm, Ingo, Extended European Search Report, dated Apr. 15, 2016, pp. 1-12, European Patent Office, Berlin, Germany.

Edgar Torres, Examination report No. 1 for standard patent application, dated Jan. 18, 2017, pp. 1-3, IP Australia, Australia.

* cited by examiner

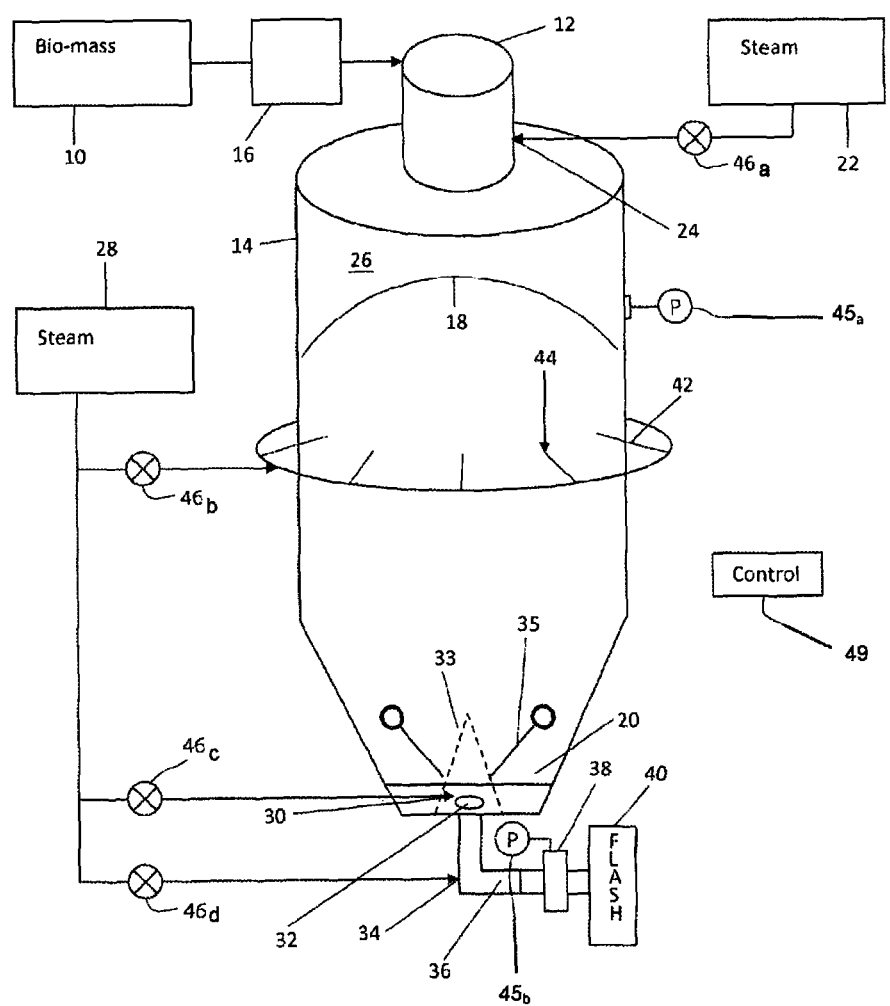

METHOD AND APPARATUS FOR ADDING STEAM FOR A STEAM EXPLOSION PRETREATMENT PROCESS

This application is related to, and claims the benefit of, U.S. Provisional Pat. App. No. 61/703,082, filed Sep. 19, 2012, and PCT International App. No. PCT/US2013/060,272, filed Sep. 18, 2013. Each of the above-identified priority patent applications is incorporated herein by reference in its entirety.

BACKGROUND OF THE INVENTION

The present invention relates to the use of steam in pressurized vertical reactor vessels and steam explosion processes to pre-treat biomass feed stocks, such as agricultural residues (including stalks, stover and hulls), straws and grasses, forest, sawmill residues (including wood chips and shredded thinnings) and lignocellulosic material, collectively referred to as biomass.

Biomass is heated and pressurized with steam in a first reactor, such as a vertical reactor vessel. As the heated biomass moves from the vertical reactor vessel, the biomass moves through an expansion valve or other expansion device to cause the biomass to undergo a steam explosion process. An exemplary steam explosion process for pretreatment of biomass is described in U.S. Pat. No. 8,057,639. A similar process for pulping of wood chips is disclosed in U.S. Patent Application Publication 2008/0277082.

Steam, besides being the source of heat and pressurization for the biomass in the vertical reactor vessel, is the propellant that moves the biomass from the vertical reactor vessel, through a discharge pipe (conduit) and towards the expansion device. The amount of steam, gas or vapor needed to propel the biomass may be significant, such as 50 to 500 kilograms of steam to bone-dry ton (kgs/BDT) of biomass. The amount of steam may be injected at an elevation corresponding to the lower region of the vertical reactor vessel and may be needed to propel the biomass is typically dependent on the process, rate and volume of biomass moving through the vertical reactor vessel, and the dimensions and conditions of the vertical reactor vessel and related equipment.

Horizontal reactor vessels effectively use steam to propel biomass from the horizontal reactor vessel towards a steam explosion device. Steam added to the inlet of a horizontal reactor vessel remains in the horizontal reactor vessel and above the biomass. While some of the steam condenses in the horizontal reactor vessel, some of the steam also remains as a gas applying pressure to the biomass along the entire length of the horizontal reactor vessel. Because the steam in a horizontal reactor vessel extends the length of the horizontal reactor vessel and is immediately above the biomass at the outlet end of the horizontal reactor vessel, the steam propels the biomass through the outlet of the horizontal reactor vessel without disrupting the flow of biomass in the horizontal reactor vessel.

Conventional vertical reactor vessels have a disadvantage as compared to horizontal reactor vessels with respect to steam explosion pulping. Steam is added to the inlet at the upper end of a vertical reactor vessel. The steam is added to heat the biomass, pressurize the vertical reactor vessel and propel the biomass out a bottom discharge of the vertical reactor vessel. To propel the biomass, the steam must pass down through the biomass in the vertical reactor vessel to reach the bottom outlet. A relatively large amount of extra steam is required to ensure that sufficient steam is still present to propel the biomass out of the conventional vertical reactor system. In a vertical reactor vessel, steam moving down through the biomass may form gas passages, e.g., a rat-holing effect, through the biomass. These passages may cause the biomass to experience uneven retention periods in the vertical reactor vessel and affect the quality of the process.

In some respects, vertical reactor vessels are more efficient than horizontal reactor vessels. Vertical reactor vessels more efficiently use their volume because biomass occupies a greater portion of a vertical reactor vessel than is occupied by biomass in a horizontal reactor vessel. Vertical reactor vessels typically may be built much larger than horizontal reactor vessels and, thus, have a greater capacity for biomass throughput than a horizontal reactor vessel.

SUMMARY OF INVENTION

A method and apparatus have been invented to add steam to a lower region of a pressurized vertical reactor vessel system to propel biomass from the vertical reactor system. The vertical reactor system includes: a vertical reactor vessel; at least one source of steam; a source of biomass feed stock (biomass); an expansion device outside of the vertical reactor vessel; a conduit for carrying the biomass discharged from the vertical reactor vessel to the expansion device; and multiple steam injection locations within the vertical reactor vessel such as at the top, between the top and the bottom and at or near the bottom of the vertical reactor vessel, as well as steam injection to the conduit for carrying the biomass discharged from the vertical reactor vessel to the expansion device to propel the biomass through the vertical reactor vessel system.

To avoid having to pass large amounts of steam through an entire column of biomass in a vertical reactor vessel, steam may be added to the vertical reactor vessel system at, near, or after the bottom outlet of the vertical reactor vessel. The added steam propels the biomass from the vertical reactor vessel to an expansion device, such as a steam explosion device.

The steam needed to propel the biomass is added to the lower regions of the vertical reactor vessel system. Steam added to the upper regions of the vertical reactor vessel serves to heat and pressurize the biomass in the vertical reactor vessel. Further, steam may be added at other elevations of the vertical reactor vessel, such as a middle elevation or region, between the upper and lower regions, to control compaction (e.g. obtain a desired compaction) of the biomass in the vertical reactor vessel.

By reducing or eliminating the addition of propelling steam at the upper region of the vertical reactor vessel, the total volume or amount of steam added to the vertical reactor vessel can be reduced and the amount of steam added at the upper region of the vertical reactor vessel may be substantially reduced. By reducing or eliminating the need to pass a sufficient amount of steam down through the entire pile to propel the biomass through a bottom outlet, the risk of steam passages forming in the pile, e.g., rat-holes, is minimized. Reducing or eliminating rat-holes aids in providing uniform treatment of the biomass and achieving a uniform retention period of all biomass passing through the vertical reactor vessel.

By adding steam at two or more elevations in the vertical reactor vessel system, the volume or rate of steam added may be regulated to achieve biomass heating and pressurizing at the upper regions of the vertical reactor vessel and to propel the biomass from the bottom of the vertical reactor vessel system. Adding steam at two or more elevations of a vertical reactor vessel, avoids having to inject a large amount of steam at the top of the vessel and forcing large amounts of the steam down through the pile of biomass to provide propelling steam at the bottom of the vertical reactor vessel system.

While steam may be the preferred gas to be used for heating (or cooling or both) and pressurizing or as the pressurizing gas for the biomass, other gases may also be used. Other gases may include air, nitrogen, oxygen, argon or other inert gases.

A method has been conceived for treating cellulosic biomass feed stock including: feeding the feed stock through a pressure isolation device and to an upper inlet of a vertical reactor vessel, wherein the feed stock is deposited on a pile of feed stock within the vertical reactor vessel; adding heat energy to heat and pressurize the feed stock by injecting a first steam volume to an upper region of the vertical reactor vessel; propelling the feed stock through an outlet in a lower region of the vertical reactor vessel system by injecting at least a second steam volume into the biomass at an elevation corresponding to the lower region of the vertical reactor vessel at, near or just below the bottom outlet of the vertical reactor vessel, wherein the injection of the first steam volume and the injection of the at least second steam volume are vertically separated by at least a portion of the biomass column, and moving the propelled feed stock through an expansion device, such as a steam explosion device, to subject the feed stock to a steam explosion process. In some embodiments, the first steam volume and the at least second steam volume may have the same source. Some embodiments may have the injection of the at least second steam volume, propelling steam, after the bottom outlet of the vertical reactor vessel directly into a conduit for the feed stock extending from the bottom outlet of the vertical reactor vessel to the expansion device where the biomass is discharged from the vertical reactor vessel and propels the biomass through the conduit connecting the bottom of the vertical reactor vessel and the expansion device.

A method has been conceived for treating biomass comprising: adding biomass through a pressure isolation device and to an upper inlet of a vertically oriented reactor vessel, wherein the biomass falls through a vapor phase within the vertically oriented reactor vessel and lands on a pile of biomass in the vertically oriented reactor vessel; injecting a heated and pressurized gas or vapor to an upper region of the vertically oriented reactor vessel; injecting at least one pressurized gas or vapor through nozzles at, near or after a lower region of the vertically orientated reactor vessel system such that there is a vertical distance between the injection of the heated and pressurized gas or vapor and the at least one pressurized gas or vapor, wherein the at least one pressurized gas or vapor propels the biomass in the vertical reactor vessel from the vertical reactor vessel through an expansion device (such as a steam explosion device), and rapidly reducing the pressure on the biomass in the expansion device to burst cellular structures in the biomass. In some embodiments, the gas used to propel the biomass from the bottom outlet of the vertical reactor vessel to the expansion device is injected into the conduit after the bottom outlet of the vertical reactor vessel.

An assembly has been conceived for treating biomass feed stock comprising: a vertical reactor vessel system including an upper feed stock inlet of a vertical reactor vessel and an upper steam inlet; a feed stock outlet in the lower region of the vertical reactor vessel; a propelling steam inlet at an elevation corresponding to the lower region of the vertical reactor vessel system, wherein the upper steam inlet and the propelling steam inlet are vertically separated by a height of biomass; an expansion device, such as a steam explosion device, configured for receiving the feed stock from the vertical reactor vessel, and a conduit extending from the feed stock outlet to the expansion device.

BRIEF DESCRIPTION OF THE DRAWINGS

The FIG. 1 depicts a schematic diagram of a flow through a steam explosion process including a vertical reactor vessel and process.

DETAILED DESCRIPTION OF THE INVENTION

The FIG. 1 shows an exemplary flow for a steam explosion process for biomass. A source 10 of biomass, such as a feed stock bin, provides the biomass to an upper inlet, such as a top separator device 12, of a vertical reactor vessel 14.

The vertical reactor vessel 14 may be generally cylindrical and have a height of over 100 feet (33 meters), a diameter of over 20 feet (7 meters) and a capacity to continuously process over 500 tons of biomass per day. The vertical reactor vessel 14 may also be pressurized such as to a pressure of up to 35 bar gauge (barg), such as in a range of 3 barg to 35 barg (300 kPa to 3,500 kPa). The steam added to the vertical reactor vessel 14 controls the pressure in the vertical reactor vessel 14.

A biomass feed system 16 transports the biomass from the source 10 to the upper inlet 12. The biomass feed system 16 may include screw conveyors and conduits. Liquid, e.g., water, may be added to the biomass to form a slurry that flows through the conduits and equipment of the feed system 16 and to the upper inlet 12 of the vertical reactor vessel 14.

A pressure isolation device (not shown), such a rotary valve, plug screw feeder, lock-hopper system, high pressure feeder or pump(s), may be located between the biomass feed system 16 and the upper inlet 12 and ensures that the pressure in the vertical reactor vessel 14 is not released as the slurry of biomass and liquid enters the vertical reactor vessel 14.

As the slurry enters the vertical reactor vessel 14, the biomass moves, e.g., falls, from the upper inlet to a pile 18, e.g., a column, of biomass contained in the vertical reactor vessel 14. The pile 18 of biomass extends from an upper region of the interior of the vertical reactor vessel 14 to a lower discharge region 20.

The biomass continuously enters the upper inlet 12, falls to the pile 18 and is continuously discharged through the bottom outlet 32 of the vertical reactor vessel 14. Biomass is continually being added to and depleted from the pipe at the same rate such that the upper surface of the pile 18 remains generally at the same elevation in the vertical reactor vessel 14.

A steam source 22 provides steam to pressurize the vertical reactor vessel 14 and add heat energy to the biomass. The steam may be injected through injection inlets 24, e.g., nozzles, in the upper region of the vertical reactor vessel 14. The steam may also be injected through a mixing device (not shown) between the pressure isolation device and the upper inlet 12 of the vertical reactor vessel 14.

The rate or volume of steam added at the upper region of the vertical reactor vessel 14 may be limited to that needed to heat the biomass and pressurize the vertical reactor vessel 14. The steam injection may form a hot vapor region 26 in the vertical reactor vessel 14 and above the pile 18. While some steam may flow down into the pile 18, it need not be a requirement that steam be added to the hot vapor region 26 in sufficient amounts to pass down through the pile 18 and out the bottom of the vertical reactor vessel 14.

An additional source of steam 28 (which may be the same source of steam 22) provides steam to one or more steam injection devices at middle elevations and lower elevations (or middle region and lower region) of the vertical reaction vessel. The steam injection devices may be nozzles mounted to the sidewall of the vertical reaction vessel 14 and steam pipes extending along the axis of the vertical reaction vessel 14.

The steam injection devices may be arranged at one or more elevations of the vertical reactor vessel 14. Steam injected through these devices affects the density and consistency of the biomass near the steam injection. For example, steam is injected to reduce the solids consistency at middle and lower elevations in the vertical reactor vessel 14. Similarly, steam may be injected to agitate and mix the biomass and ensure a uniform distribution of biomass at each elevation in the vertical reactor vessel 14.

The density and consistency of the biomass at each elevation of the pile 18 is preferably uniform across a cross-section of the vertical reactor vessel 14. A uniform consistency of the biomass promotes uniform treatment of the biomass in the vertical reactor vessel 14.

The second source of steam 28 may provide steam at a volumetric rate selected to propel the biomass into the bottom outlet 32. The rate of propelling steam may differ from the pressure and rate of the heating steam added at the upper region of the vertical reactor vessel. The rate or amount of steam supplied for propelling the biomass may be in a range of 50 to 500 kilograms of steam to bone-dry ton (kgs/BDT) of biomass.

A lower steam injection inlet or nozzle 30 may inject the propelling steam into the vertical reactor vessel 14 at or near the bottom outlet 32 for biomass. The lower steam injection inlet or nozzle 30 may be mounted to the sidewall of the vertical reactor vessel 14 in a region near the bottom outlet 32, or may be mounted on the bottom of the vertical reactor vessel 14 and near the bottom outlet 32. The lower steam injection inlet or nozzle 30 may be, for example, an annular array of nozzles arranged around the circumference of the vertical reactor vessel 14 at an elevation corresponding to a biomass movement device 33. Steam injected through the lower steam injection inlet or nozzle 30 assists in moving (propelling) biomass through the bottom of the vertical reactor vessel 14 and from the bottom outlet 32.

The biomass movement device 33 in the lower discharge region 20 of the vertical reactor vessel 14 may include a convergence section, such as one-dimensional convergence of the vertical reactor vessel at, near or above an elevation corresponding to the propelling steam inlet, to provide uniform movement of the biomass through the bottom of the vertical reactor vessel and to the bottom outlet 32 at the bottom of the vertical reactor vessel 14. The convergence section may be a DIAMONDBACK® convergence section sold by the Andritz Group and described in U.S. Pat. Nos. 5,500,083; 5,617,975 and 5,628,873. In some embodiments the propelling steam inlet is at a location after (vertically below) the bottom outlet of the vertical reactor vessel at the conduit extending from the bottom outlet of the vertical reactor vessel to the expansion device. Additionally, the biomass movement device 33 may include a stirring device having stirring arms 35 to assist in moving the biomass within the vertical reactor vessel 14 and to the bottom outlet 32.

Other arrangements of steam injection nozzles 24, 30 and 44, may include a center pipe extending vertically along the axis of the vertical reactor vessel, nozzles included with the stirring device and nozzles oriented to direct steam to propel the biomass into the bottom outlet 32.

Steam 28, an at least second steam injection, (could also be a gas or vapor as described previously) may also be injected through a nozzle 34 oriented to inject steam directly into a conduit 36, e.g., pipe, below the bottom outlet 32 of the vertical reactor vessel 14. Injecting steam 28 (propelling steam) directly into a conduit 36, extending from the bottom outlet 32 of the vertical reactor vessel 14 through nozzle 34 will propel the biomass from the vertical reactor vessel 14 to the expansion device 38. By adding steam 28 into conduit 36 using nozzle 34, there is less likelihood of a hole being made in the biomass from the steam 28 propelling the biomass in conduit 36 to the expansion device 38.

The biomass from the vertical reactor vessel 14 is propelled through the conduit 36 passes through an expansion device 38 and to a flash vessel 40. The expansion device 38 may be a conventional steam explosion device used for biomass or pulping. The flash vessel 40 receives the biomass after the expansion device 38 subjects the biomass to a sudden expansion such as a steam explosion process.

Steam 22, 28 may be added to the pile of biomass at elevations of the vertical reactor vessel 14 between the upper inlet region and the bottom discharge region. For example, a circular array 42 of nozzles around the vertical reactor vessel 14 may be at the middle height and the lower one-quarter or sixth of the height of the vertical reactor vessel 14. The additional steam may assist in moving the biomass towards the bottom outlet 32 of the vertical reactor vessel 14. Additionally, steam may be introduced at other elevations of the vertical reactor vessel 14 to provide enhanced control of the transfer of heat energy to the biomass in the pile and thereby provide additional means for regulating the temperature of the pile. The steam injected at or near the bottom of the vertical reactor vessel 14 using lower steam injection inlet or nozzle 30 may be solely for discharging the biomass through the bottom outlet 32.

Further, injecting steam at various elevations of the vertical reactor vessel 14 provides a means for regulating and controlling the pressure differential from the top to bottom of the biomass pile, e.g., column, and control the compaction and flow of biomass in the vertical reactor vessel 14.

The injecting of steam at various levels of the vertical reactor vessel 14 also allows for a system to control the steam for propelling the biomass from the vertical reactor vessel 14 to the expansion device 38. The system to control the steam for propelling the biomass relies on the differential pressure measurement made between the vapor space 26 at top of the vertical reactor vessel 14 and the vapor space within or above the upper region of the expansion device 38. The differential pressure measurement device may be made using a conventional device (dp cell) where the signal from the dp cell is used to control the position of the control valve to control the flow of steam 28 entering at conduit 36 through nozzle 34 for propelling the biomass to the expansion device 38.

A control system 49 may be used to regulate the addition of steam at the various elevations of the vessel. The control system 49 may include vapor pressure sensors $45_a$, $45_b$ and steam valves $46_a$, $46_b$, $46_c$, $46_d$. The pressure sensors $45_a$, $45_b$ monitor the vapor pressure in the hot vapor section 26 at the top of the vessel 14 and in a vapor space in the expansion device 38. The control system 49 may be manual in which a technician monitors the pressure sensors $45_a$, $45_b$ and adjusts the valves $46_a$, $46_b$, $46_a$, $46_d$. The control system 49 may also include controllers, e.g., a computer system, that monitors the pressure sensors $45_a$, $45_b$ and adjusts the valves $46_a$, $46_b$, $46_c$, $46_d$ to achieve desired pressure differences between the pressure in the hot vapor region 26 and the vapor space of the expansion device 38. The desired pressure differences may be stored in memory of the computer system and called from memory as the computer system executes a program stored in memory for controlling the steam injection by adjusting the valves $46_a$, $46_b$, $46_c$, $46_d$.

The differential pressure between the hot vapor region 26 and the vapor space in the expansion device 38 may be controlled to less than +/−100 kPa (+/−1 bar) of zero, or less than +/−50 kPa (+/−0.5 bar) of zero, or less than +/−30 kPa (+/−0.3 bar) of zero. A slight positive pressure differential in the hot vapor region 26 as compared to the vapor space of the expansion device 38 may aid in the movement of biomass through the vertical reactor vessel 14 and increase the compaction of the biomass in the vertical reactor vessel 14. A slight negative differential pressure will slow down the biomass movement within the vertical reactor vessel 14 and reduce the compaction of the biomass. By controlling the steam injection to the vessel to achieve a slight positive differential pressure or a slight negative differential pressure, provides a means to control the operating conditions in the vertical reactor vessel 14 and may assist in uniformly treating the biomass in the vessel. A control system for steam addition as described aids in ensuring an even flow velocity and compaction of the biomass pile, which also ensures good control of the biomass retention time in the reactor.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for treating biomass comprising:
feeding a biomass feed stock through a pressure isolation device and to an upper inlet of a vertical reactor vessel-system, wherein the biomass feed stock is deposited on a pile of biomass within a vertical reactor vessel, and wherein the feeding of the biomass feed stock to the upper inlet is continuous;
adding heat energy to heat and pressurize the biomass feed stock by injecting a first steam volume into an upper region of the vertical reactor vessel;
propelling a heated biomass from the pile of biomass through an outlet disposed at a lower region of the vertical reactor vessel by injecting at least a second steam volume into the lower region of the vertical reactor vessel at, near, or after the outlet of the vertical reactor vessel to define a propelled heated biomass, wherein the injection of the first steam volume and the injection of the at least the second steam volume are vertically separated by at least a portion of the pile of biomass;
moving the propelled heated biomass to and through an expansion device to subject the propelled heated biomass to a steam explosion process;
measuring a differential pressure between a vapor space above the pile of biomass in the vertical reactor vessel and a vapor space within or above the expansion device; and
controlling a flow of the at least the second steam volume into the lower region of the vertical reactor vessel at, near, or after the outlet of the vertical reactor vessel to regulate the moving of the propelled heated biomass to and through the expansion device based on the differential pressure.

2. The method of claim 1 further comprising adding propelling steam after the outlet of the vertical reactor vessel directly into a conduit for the propelled heated biomass, the conduit extending from the outlet of the vertical reactor vessel to the expansion device.

3. The method of claim 1 further comprising injecting additional steam into the vertical reactor vessel at a middle region between the upper and lower regions.

4. A method for treating biomass comprising:
adding a biomass through a pressure isolation device and into an upper inlet of a vertically oriented reactor vessel, wherein the biomass falls through a vapor phase within the vertically oriented reactor vessel and lands on a pile of biomass in the vertically oriented reactor vessel, and wherein the adding of the biomass into the upper inlet is continuous;
injecting a first heated and pressurized gas or vapor to an upper region of the vertically oriented reactor vessel;
injecting at least a second pressurized gas or vapor through nozzles after a lower region of the vertically oriented reactor vessel, wherein a vertical distance and at least a portion of the pile of biomass separates the injection of the first heated and pressurized gas or vapor and the injection of the at least the second pressurized gas or vapor, wherein the at least the second pressurized gas or vapor is injected into a conduit to propel the biomass to a steam expansion device, and wherein the conduit extends from the outlet of the vertically oriented reactor vessel to the expansion device,
rapidly reducing the pressure on the biomass in the expansion device to burst cellular structures in the biomass;
measuring a differential pressure between a vapor space above the pile of biomass in the vertically oriented reactor vessel and a vapor space within or above the expansion device; and
using a control system to control a flow of the at least the second pressurized gas or vapor through nozzles after a lower region of the vertically oriented reactor vessel based on the differential pressure to thereby regulate a flow of the biomass to and through the expansion device.

5. The method of claim 4, wherein the heated and pressurized gas or vapor is selected from the group consisting of: steam, air, nitrogen, oxygen, argon and other inert gas.

6. The method of claim 4, wherein the at least the second pressurized gas or vapor is selected from the group consisting of: steam, air, nitrogen, oxygen, argon and other inert gas.

7. The method of claim 4 further comprising injecting additional steam into the vertically oriented reactor vessel at a middle region between the upper and lower regions.

8. An assembly for treating biomass comprising:
a vertical reactor vessel including an upper biomass inlet and an upper steam inlet at an upper region of the vertical reactor vessel, wherein the vertical reactor vessel is configured to receive a biomass continuously;
an outlet in the lower region of the vertical reactor vessel;

a propelling steam inlet at the lower region of the vertical reactor vessel, wherein the upper steam inlet and the propelling steam inlet are vertically separated-by a height of biomass;

an expansion device configured for receiving a heated biomass from the vertical reactor vessel, and a conduit extending from the outlet to the expansion device;

sensors configured to detect a differential pressure between a vapor space above a pile of biomass in the vertical reactor vessel and a vapor space within or above the expansion device; and a control system configured to control the flow of the propelling steam based on the differential pressure.

9. The assembly of claim 8 further comprising a one-dimensional convergence section of the vertical reactor vessel at, near, or above the propelling steam inlet.

10. The assembly of claim 8, wherein the propelling steam inlet is at a location after the outlet of the vertical reactor vessel at the conduit extending from the outlet to the expansion device.

11. The assembly of claim 8 further comprising an additional steam inlet on or in the vertical reactor vessel at a middle elevation between the upper and lower regions.

12. The assembly of claim 8 wherein the expansion device is a steam explosion device.

13. The assembly of claim 8 further comprising a source of steam for the upper steam inlet and a source of steam for the propelling steam inlet.

14. The assembly of claim 13, wherein the source of steam for the upper steam inlet and a source of steam for the propelling steam inlet is the same source.

15. The method of claim 1, wherein the propelling of the heated biomass through the steam expansion device is continuous.

16. The method of claim 4, wherein rapidly reducing the pressure on the biomass in the expansion device to burst cellular structures in the biomass occurs continuously.

17. The assembly of claim 8, wherein the control system is further configured to discharge the biomass from the steam expansion device continuously.

18. A method for treating biomass comprising:
feeding a biomass feed stock through a pressure isolation device and to an upper inlet of a vertical reactor vessel-system, wherein the biomass feed stock is deposited on a pile of biomass within a vertical reactor vessel, and wherein the feeding of the biomass feed stock to the upper inlet is continuous;

adding heat energy to heat and pressurize the biomass feed stock by injecting a first steam volume into an upper region of the vertical reactor vessel;

propelling a heated biomass from the pile of biomass through an outlet disposed at a lower region of the vertical reactor vessel by injecting at least a second steam volume into the lower region of the vertical reactor vessel at, near, or after the outlet of the vertical reactor vessel to define a propelled heated biomass, wherein the injection of the first steam volume and the injection of the at least the second steam volume are vertically separated by at least a portion of the pile of biomass;

moving the propelled heated biomass to and through an expansion device to subject the propelled heated biomass to a steam explosion process, wherein the propelling steam inlet is at a location after the outlet of the vertical reactor vessel at the conduit extending from the outlet to the expansion device.

19. The method of claim 18 further comprising a source of steam for the upper steam inlet and a source of steam for the propelling steam inlet.

20. The method of claim 19, wherein the source of steam for the upper steam inlet and a source of steam for the propelling steam inlet is the same source.

21. An assembly for treating biomass comprising:
a vertical reactor vessel including an upper biomass inlet and an upper steam inlet at an upper region of the vertical reactor vessel;

an outlet in the lower region of the vertical reactor vessel;

a propelling steam inlet at the lower region of the vertical reactor vessel, wherein the upper steam inlet and the propelling steam inlet are vertically separated by a height of biomass;

an expansion device configured for receiving a heated biomass from the vertical reactor vessel, and a conduit extending from the outlet to the expansion device, wherein the propelling steam inlet is at a location between the outlet of the vertical reactor vessel and the expansion device.

* * * * *